(12) United States Patent
Gunther et al.

(10) Patent No.: US 12,085,572 B2
(45) Date of Patent: Sep. 10, 2024

(54) PROTEIN CAPTURE MEMBRANE AND METHOD OF USE THEREOF

(71) Applicant: YALE UNIVERSITY, New Haven, CT (US)

(72) Inventors: Erik Gunther, Branford, CT (US); Mikhail Kostylev, New Haven, CT (US); Stephen Strittmatter, Durham, CT (US)

(73) Assignee: Yale University, New Haven, CT (US)

( * ) Notice: Subject to any disclaimer, the term of this patent is extended or adjusted under 35 U.S.C. 154(b) by 898 days.

(21) Appl. No.: 17/053,023

(22) PCT Filed: May 7, 2019

(86) PCT No.: PCT/US2019/031082
§ 371 (c)(1),
(2) Date: Nov. 4, 2020

(87) PCT Pub. No.: WO2019/217396
PCT Pub. Date: Nov. 14, 2019

(65) Prior Publication Data
US 2021/0132077 A1 May 6, 2021

Related U.S. Application Data

(60) Provisional application No. 62/668,424, filed on May 8, 2018.

(51) Int. Cl.
*G01N 33/68* (2006.01)
*B01D 57/02* (2006.01)
(Continued)

(52) U.S. Cl.
CPC ......... *G01N 33/6842* (2013.01); *B01D 57/02* (2013.01); *B01D 69/02* (2013.01);
(Continued)

(58) Field of Classification Search
CPC .. G01N 33/6842; G01N 33/551; G01N 33/68; B01D 57/02; B01D 69/02;
(Continued)

(56) References Cited

U.S. PATENT DOCUMENTS

2009/0112075 A1* 4/2009 Klok .................. A61B 5/14525
600/365
2010/0166604 A1* 7/2010 Lim ....................... G01N 31/22
977/773
(Continued)

FOREIGN PATENT DOCUMENTS

KR 20110115659 A 10/2011

OTHER PUBLICATIONS

Towbin, H. et al. "Electrophoretic transfer of proteins from polyacrylamide gels to nitrocellulose sheets: Procedure and some applications." PNAS. 76.9. 4350-4354. 1979. (Year: 1979).*

(Continued)

*Primary Examiner* — Jill A Warden
*Assistant Examiner* — Jacqueline Brazin
(74) *Attorney, Agent, or Firm* — Saul Ewing LLP; Kathryn Doyle; Justin W. Crotty

(57) ABSTRACT

In one aspect, the invention provides a protein capture membrane comprising a first side and a second side and a plurality of interstices extending contiguously from the first side to the second side, wherein the interstices are coated with a protein-reactive coating; and the porous substrate comprises nanoporous alumina or porous glass. In another aspect the invention provides a method of detecting a protein of interest in a plurality of proteins.

6 Claims, 15 Drawing Sheets

(51) Int. Cl.
   *B01D 69/02*   (2006.01)
   *B01D 69/10*   (2006.01)
(52) U.S. Cl.
   CPC .... *B01D 69/108* (2022.08); *B01D 2325/0283* (2022.08); *B01D 2325/04* (2013.01)
(58) Field of Classification Search
   CPC .... B01D 69/10; B01D 71/70; B01D 2325/02; B01D 2325/04
   USPC .......................................................... 436/86
   See application file for complete search history.

(56) References Cited

U.S. PATENT DOCUMENTS

| | | | |
|---|---|---|---|
| 2011/0053284 A1* | 3/2011 | Meller | ............ G01N 33/48721 506/13 |
| 2016/0106671 A1 | 4/2016 | Brinker et al. | |

OTHER PUBLICATIONS

Yeung, Y-G. et al. "A solution for stripping antibodies from PVDF immunoblots for multiple reprobing." Anal Biochem. 389(1). 89-91. 2009. (Year: 2009).*

Baranowka, M. et al. (2014). Protein attachment to nanoporous anodic alumina for biotechnological applications: Influence of pore size, protein size, and functionalization path. Colloid and Surface B: Biointerfaces. 122: 375-383. (Year: 2014).*

Alvarez, Jesus, et al., "Real time optical immunosensing with flow-through porous alumina membranes", Sensors and Actuators B: Chemical, Elsevier BV, NL, vol. 202; Jun. 2014; XP029009249, 834-839.

Escosura-Muniz, De La Alfredo, et al., "Nanochannels for electrical biosensing", Trac Trends in Analytical Chemistry, vol. 79, May 1, 2016 , XP055876444, 134-150.

Rajeev, Gayathri, "Advances in Nanoporous Anodic Alumina-Based Biosensors to Detect Biomarkers of Clinical Significance: A Review", Advanced Healthcare Materials, vol. 7, No. 5; Dec. 5, 2017, XP055876331, 1700904.

Schnabel, Roland, et al., "Structural and chemical properties of glass capillary membranes and their use in protein separation", Glastechnische Berichte, vol. 62, No. 2; Feb. 1989; XP000025684,, p. 24-29;57.

Supplementary Partial European Search Report, issued Jan. 31, 2022, for European App. No. 19799040.1.

International Search Report and Written Opinion issued by the International Searching Authority on Aug. 30, 2019 for PCT/US2019/031082, 11 pages.

* cited by examiner

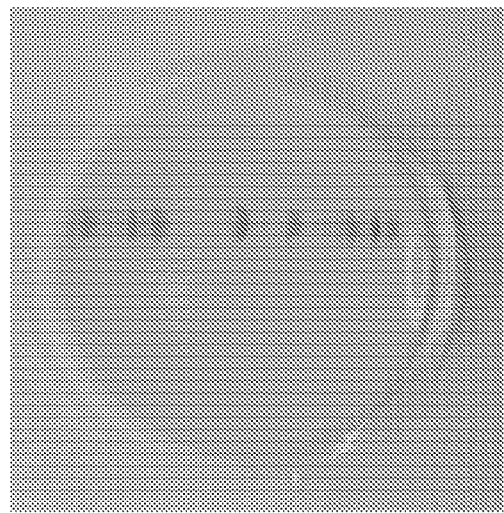
FIG. 6
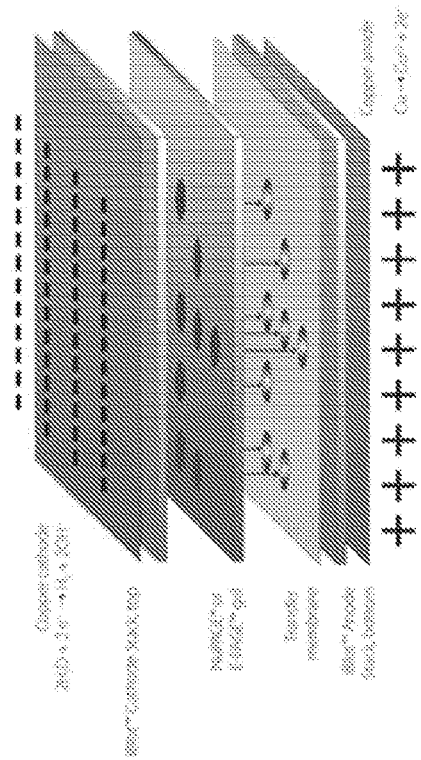

FIG. 10
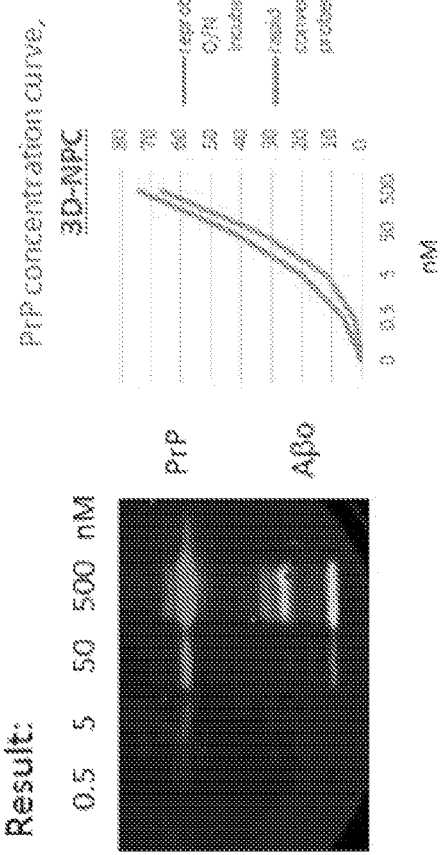
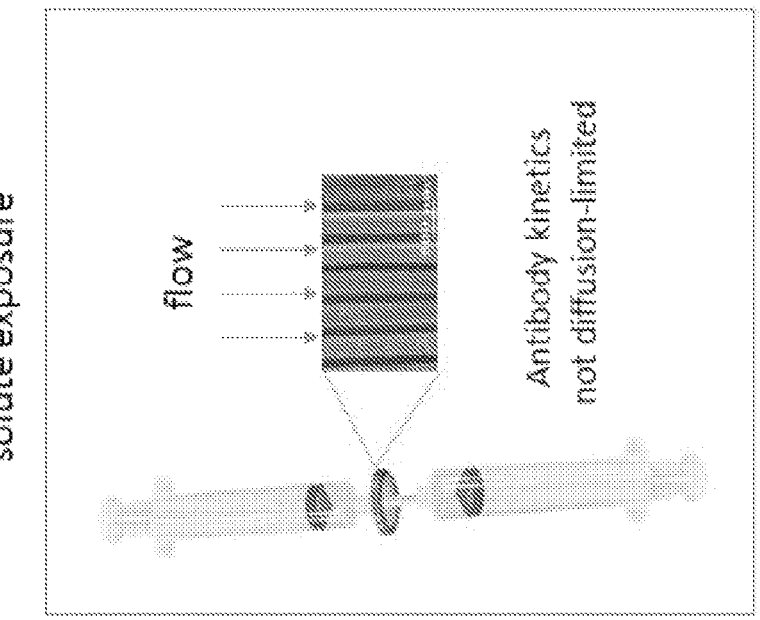

Parallel lanes (20/cm)
80 lanes/disc

3D-NPC membrane

Sealed chamber w controlled flow in out camera

Overnight throughput:

Probe cycles = 15 min x 2 antigens = 8 probes/hr 8 probes/hr x 12 hrs = 96 probes vs. western:

Single probe cycle 2 probes/12 hrs x 12 hrs = 2 probes

Human brain lysate dilution series

PROTEIN CAPTURE MEMBRANE AND METHOD OF USE THEREOF

CROSS-REFERENCE TO RELATED APPLICATIONS

The present application is a 35 U.S.C. § 371 national phase application from, and claiming priority to, International Application No. PCT/US2019/031082, filed May 7, 2019, which claims priority under 35 U.S.C. § 119(e) to U.S. Provisional Patent Application No. 62/668,424 filed May 8, 2018, which are hereby incorporated by reference in their entireties herein.

STATEMENT REGARDING FEDERALLY SPONSORED RESEARCH OR DEVELOPMENT

This invention was made with government support under AG034924, AG053000 and NS097283 awarded by National Institutes of Health. The government has certain rights in the invention.

BACKGROUND OF THE INVENTION

The absence of a practical, cost effective, high-throughput technique for proteomics creates a bottleneck in a variety of areas of biotechnology, medicine and research in general. There is a need in the art for a practical method of identifying and quantifying a large number of proteins present in complex mixtures. The present invention addresses this need.

SUMMARY OF THE INVENTION

In one aspect, the invention provides a protein capture membrane comprising a porous substrate comprising: a first side and a second side and a plurality of interstices extending contiguously from the first side to the second side, wherein the interstices are coated with a protein-reactive coating; and the porous substrate comprises nanoporous alumina or porous glass.

In various embodiments, the interstices have a diameter of about 500 nm or less than about 500 nm.

In various embodiments, the porous substrate has a thickness from the first side to the second side of about 50-100 μm.

In various embodiments, the porous substrate has a thickness from the first side to the second side of about 100 μm.

In various embodiments, the protein-reactive coating comprises a silane derivative.

In various embodiments, the silane derivative is covalently bound to the nanoporous alumina substrate.

In various embodiments, the protein-reactive coating is selected from the group consisting of:

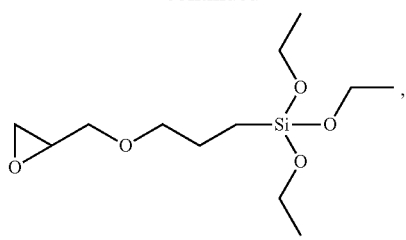

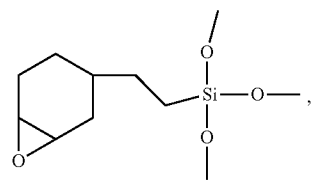

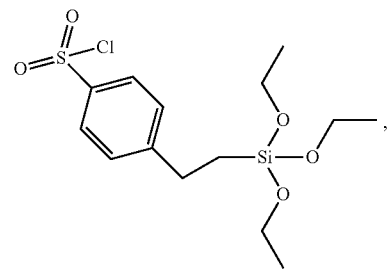

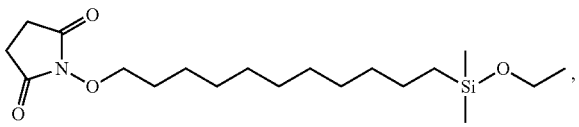

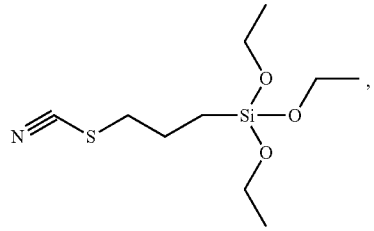

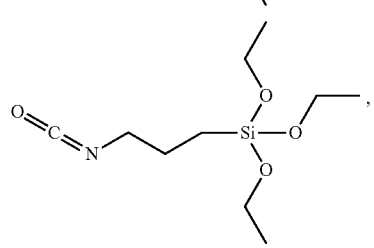

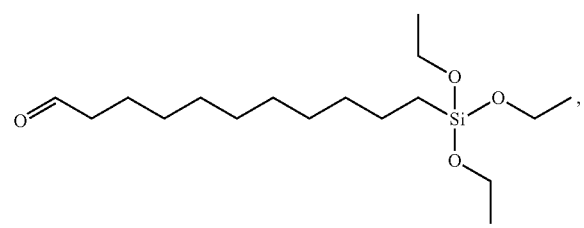 [SMILES: CCO[Si](CCCCCCCCCCC=O)(OCC)OCC]

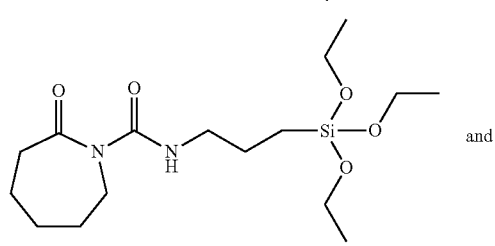

and

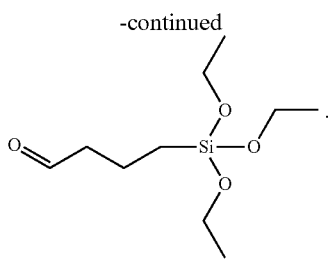

In various embodiments, the protein-reactive coating is triethoxysilylundecanal

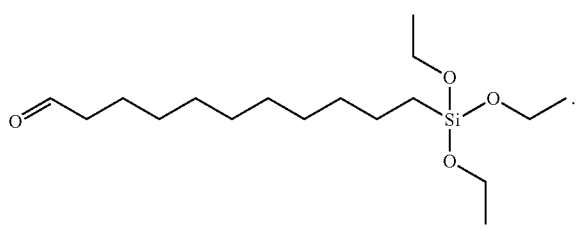 [SMILES: CCO[Si](CCCCCCCCCCC=O)(OCC)OCC]

In various embodiments, the protein-reactive coating is selected from the group consisting of 3-thiocyanatopropyltriethoxysilane, triethoxysilylundecanal, trimethoxy[2-(7-oxabicyclo[4.1.0]hept-3-yl)ethyl]silane, (3-glycidyloxypropyl)triethoxysilane, 3-isocyanatopropyltriethoxysilane, N-[5-(trimethoxysilyl)-2-aza-1-oxopentyl]caprolactam, 11-(succinimidyloxy)undecyldimethylethoxysilane, 2-(4-chlorosulfonylphenyl)ethyltrimethoxysilane and triethoxysilylbutyraldehyde.

In various embodiments, the invention provides a method of transferring at least one protein of interest in a plurality of proteins to the protein capture membrane comprising: electrophoretically transferring the at least one protein of interest to the porous substrate.

In various embodiments, the invention provides a method of transferring at least one protein of interest to the protein capture membrane, wherein the porous substrate is comprises material with intrinsic protein covalent binding character.

In another aspect, the invention provides a method of detecting at least one protein of interest in a plurality of proteins, the method comprising: contacting the plurality of proteins with a porous substrate comprising: a first side and a second side, and a plurality of interstices extending contiguously from the first side to the second side, wherein the interstices are coated with a protein-reactive coating, thereby covalently binding at least a portion of the plurality of proteins to the protein-reactive coating, exposing the covalently bound plurality of proteins to a first molecule that binds the at least one protein of interest; and detecting the first molecule that binds at least one protein of interest, thereby detecting the at least one protein of interest; wherein contacting the plurality of proteins with the porous substrate comprises electrophoretic transfer of the proteins to the porous substrate.

In various embodiments, the porous substrate comprises nanoporous alumina or porous glass.

In various embodiments, the first molecule is selected from the group consisting of an antibody, an aptamer and a protein.

In various embodiments, contacting the plurality of proteins with the porous substrate comprises: separating the plurality of proteins using electrophoresis. In various embodiments, the plurality of proteins are separated using various biochemical techniques, including but not limited to polyacrylamide gel electrophoresis, and subsequently at least a portion of the separated proteins are transferred to the porous substrate.

In various embodiments, the method further comprises: stripping the first molecule that binds at least one protein of interest and exposing the covalently bound plurality of proteins to a second molecule that binds the same or a different protein of interest; and detecting the second molecule, thereby detecting the at least one protein of interest.

In various embodiments, the second molecule is selected from the group consisting of an antibody, an aptamer and a protein.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 6. is a schematic depicting electrophoretic transfer from a gel to a protein capture membrane according to the invention.

FIG. 7A depicts a protein iblot transfer onto a 3D-nanoscale protein capture (3D-NPC) membrane with infrared fluorescence detection. FIG. 7B depicts a brain lysate iblot onto 3D-NPC membranes (ECL reaction).

FIG. 10 depicts a method for rapid immunochemistry according to an embodiment of the invention.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "stripping" is used to describe the removal of a detector molecule that specifically binds a protein of interest and may include steps of rinsing and/or preparing the sample for a second analysis. In the context of a Western blot, stripping refers to removal of an antibody, typically before probing with another antibody. As the term is defined herein, it can refer to the analogous operation with respect to any detector molecule.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Protein Capture Membrane

Figure 4:
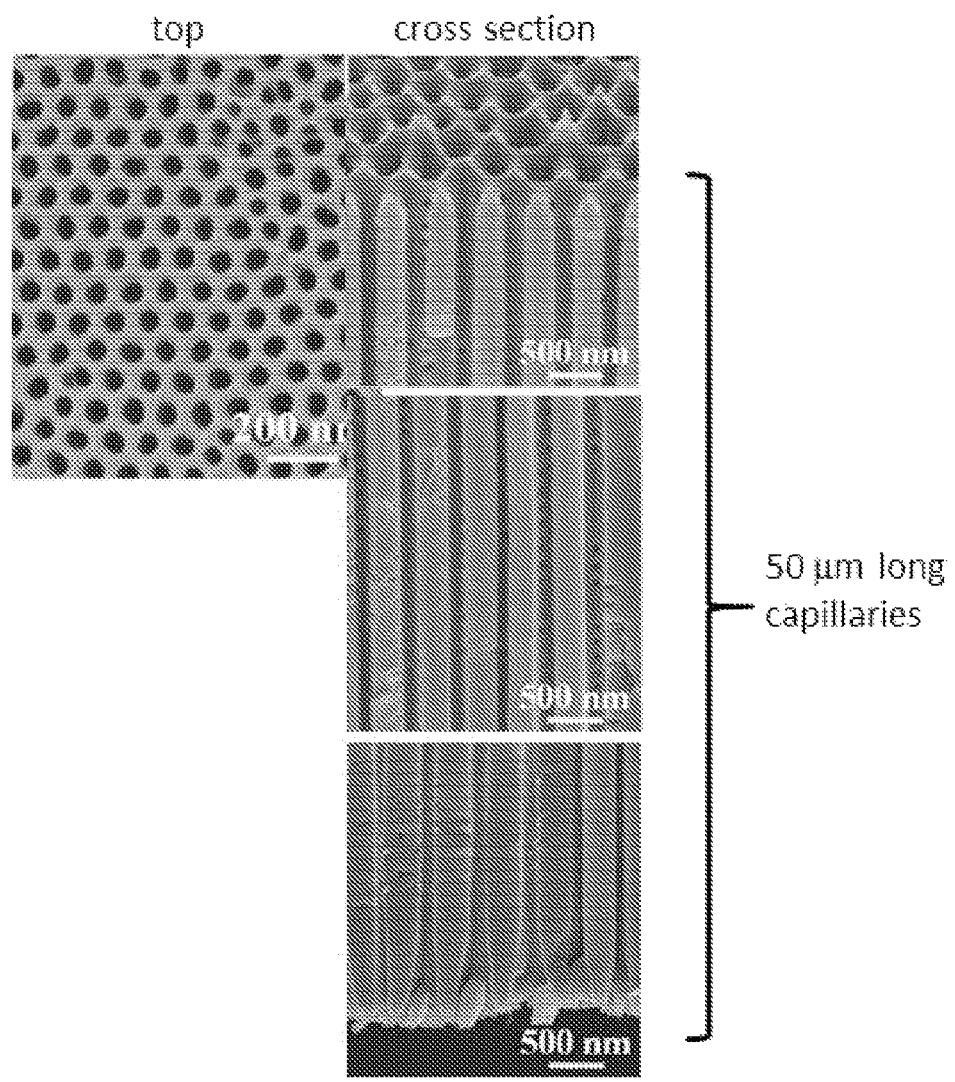
FIGS. 4A and 4B depict interstices extending from the first surface to the second surface of a porous substrate according to an embodiment of the invention in top view (FIG. 4A) and cross-section (FIG. 4B).
Figure 5:
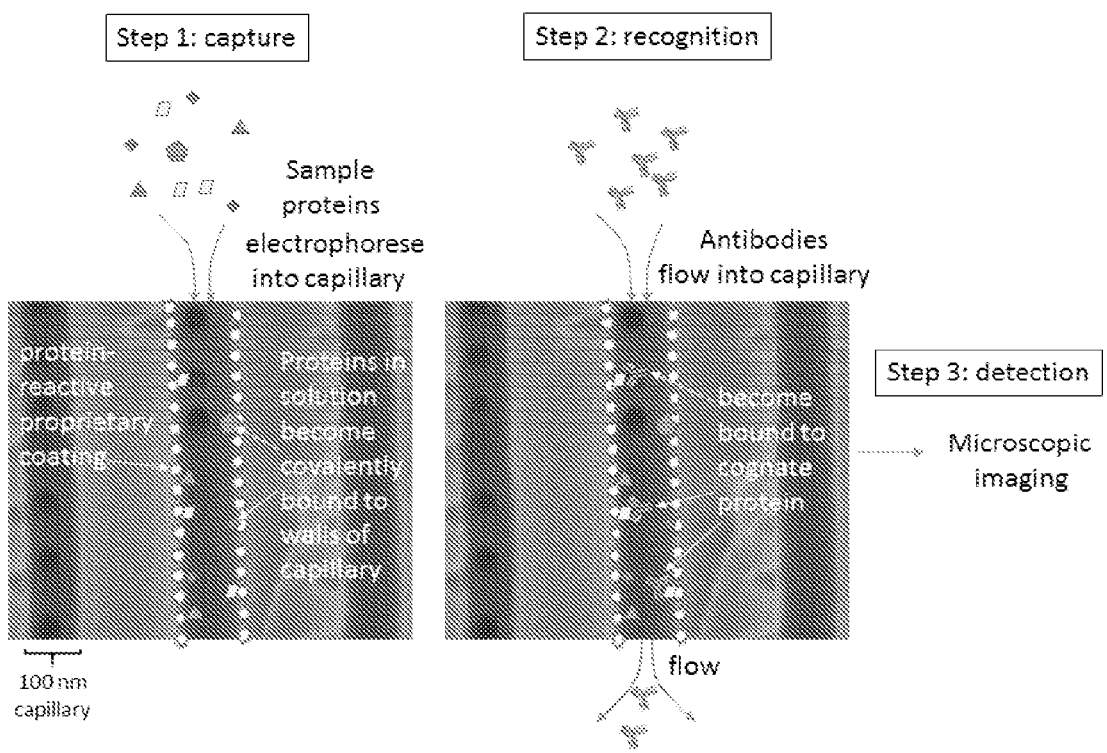
FIG. 5 is a schematic depicting an embodiment of a method of the invention using electrophoresis to load a nanoporous alumina substrate with approximately 100 nm interstices, an antibody to detect a protein of interest and microscopic imaging to detect the antibody and thereby the protein of interest.
Figure 7A:
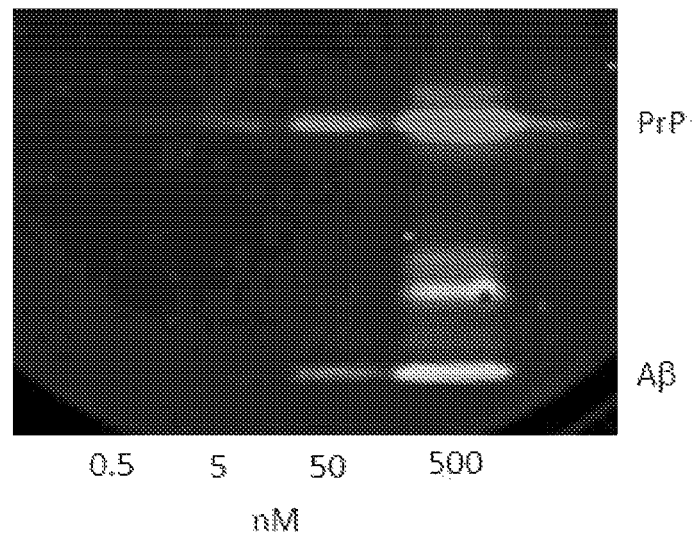
FIGS. 7A and 7B depict Western immunochemistry on an embodiment of the invention.
Figure 7B:
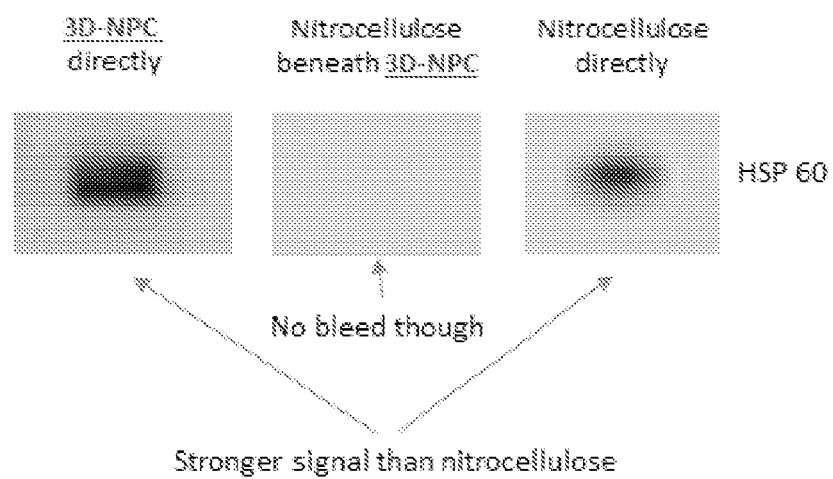
Figure 8:
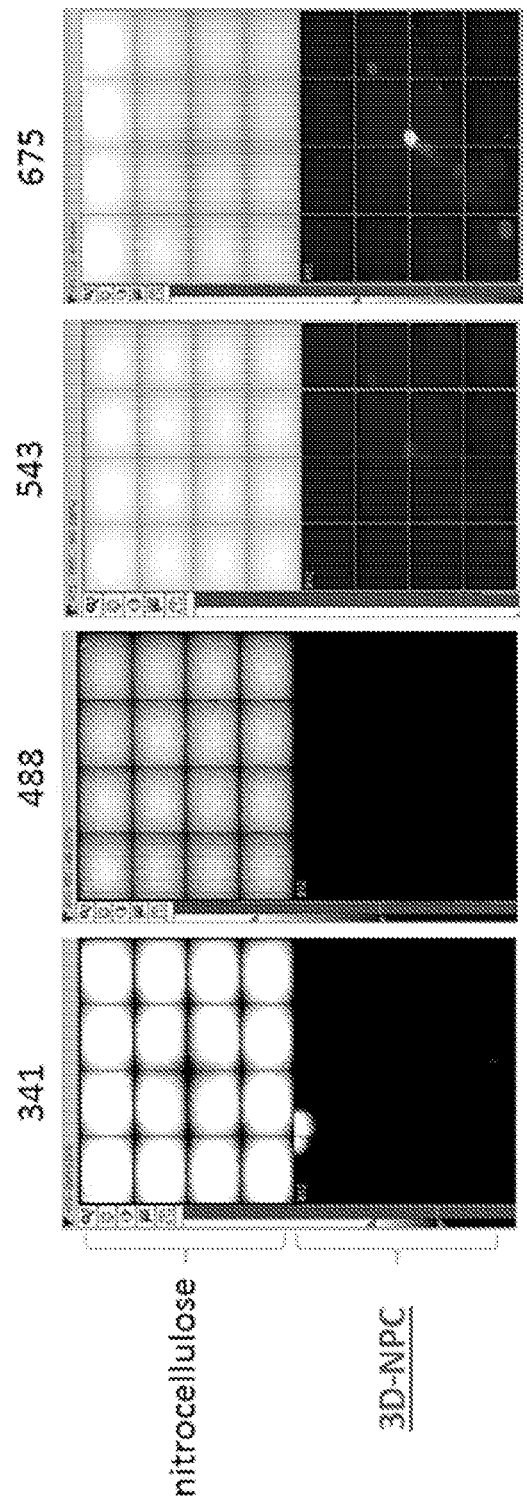
FIG. 8 depicts infrared (IR) fluorescence of an embodiment of the invention compared to nitrocellulose.
Figure 9:
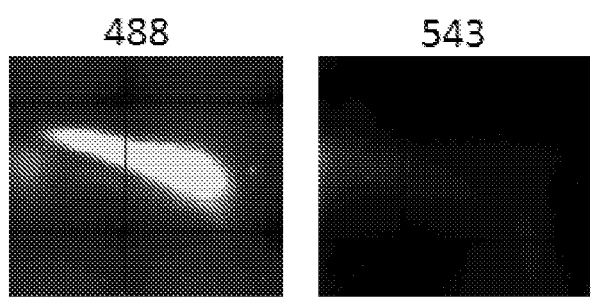
FIG. 9 depicts an immunoblot in the visible spectrum using an embodiment of the invention.
Figure 11A:
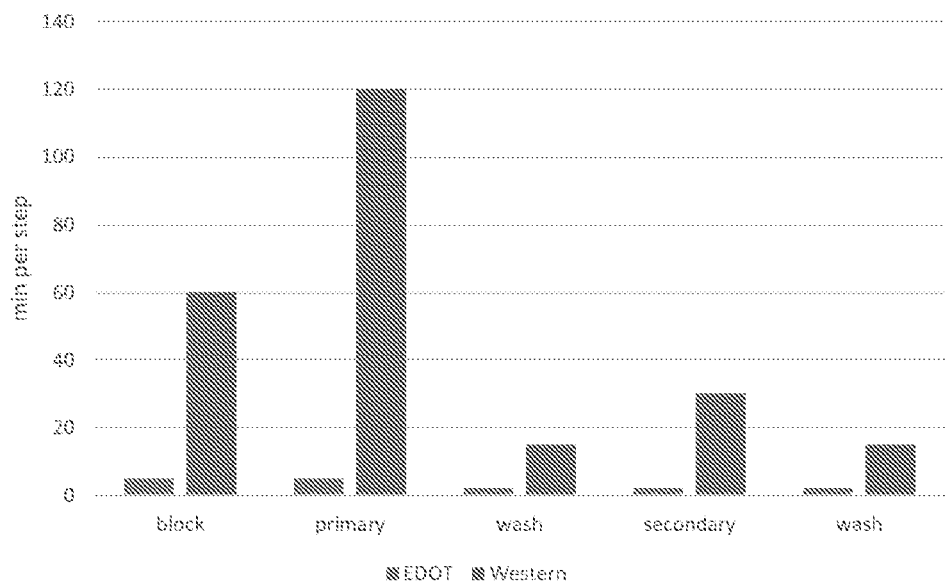
FIGS. 11A and 11B depict the relative time required for protein detection using a Western blot and an embodiment of the method of the invention, step-by-step (FIG. 11A) or total (FIG. 11B).
Figure 11B:
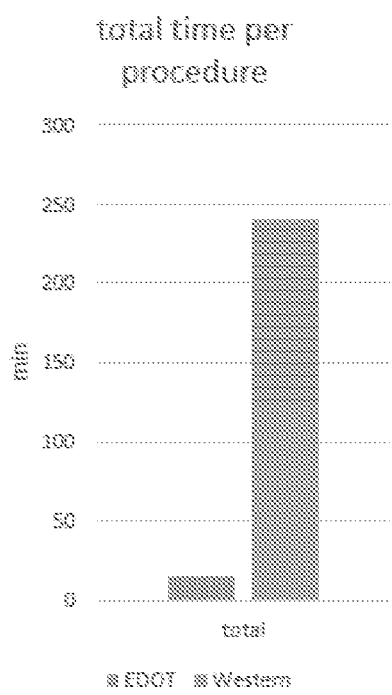
Figure 12:
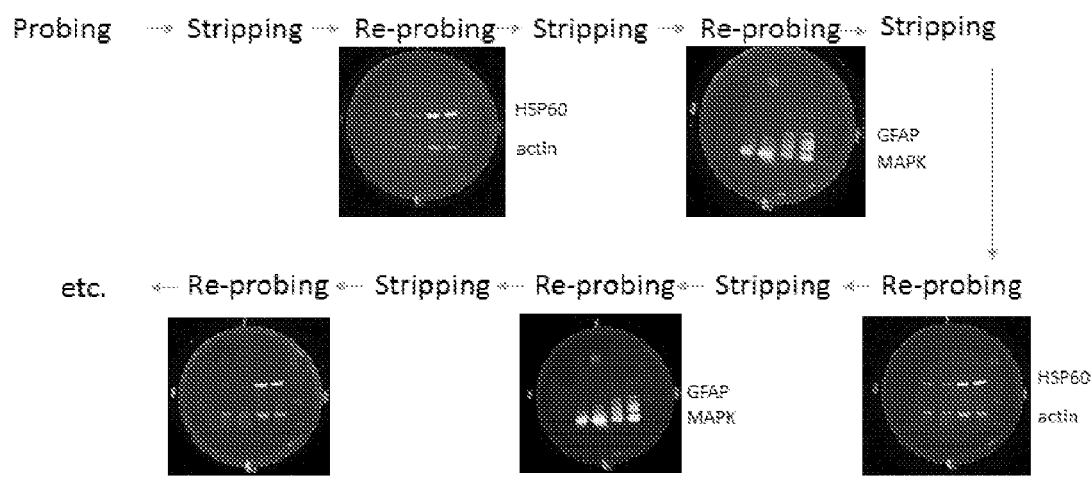
FIG. 12 depicts porous alumina membranes (200 nm pore size, 47 mm diameter) etched with piranha solution, coated with 2% tiethoxysilylundecanal in THF. Proteins transferred from gel onto derivatized porous glass fiber by electrophoresis, probed with distinct sets of antibodies against specific protein antigens (HSP60, actin, GFAP, MAPK). Proteins are transferred and bound effectively to derivatized alumina membranes, able to be probed and detected with specific antibody.

In one aspect, the invention provides a protein capture membrane comprising a porous substrate comprising a first side and a second side and a plurality of interstices extending contiguously from the first side to the second side, wherein the interstices are coated with a protein-reactive coating. Porous, as applied to the substrate, refers to the interstices extending through the substrate from one side to another. The first and second sides refer to the opposite sides of the substrate, for example, FIG. 4A depicts a first side or a second side of an embodiment of the invention. FIG. 4B depicts a cross-section showing the interstices extending contiguously from the first side to the second side.

Figure 1:
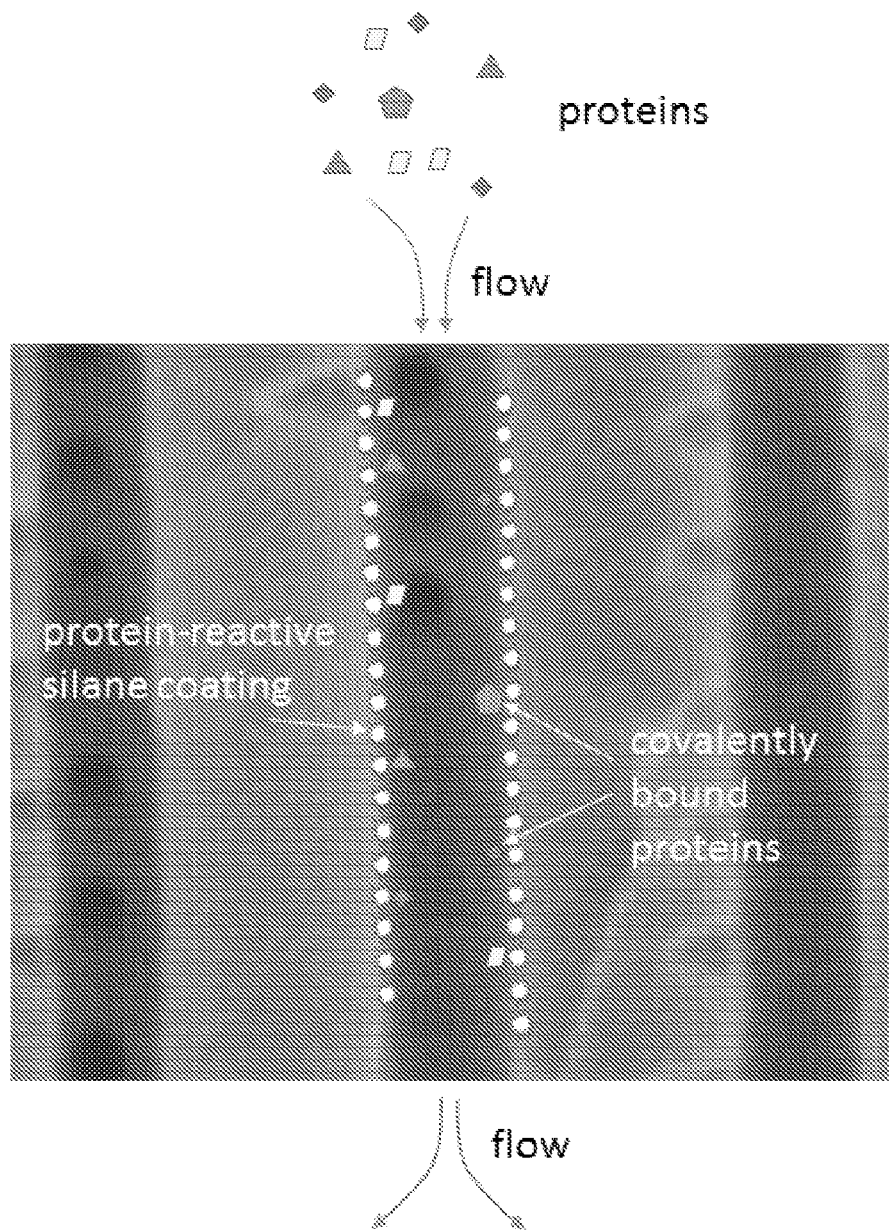
FIG. 1 depicts a schematic illustrating binding of proteins to an embodiment of the invention.
Figure 2:
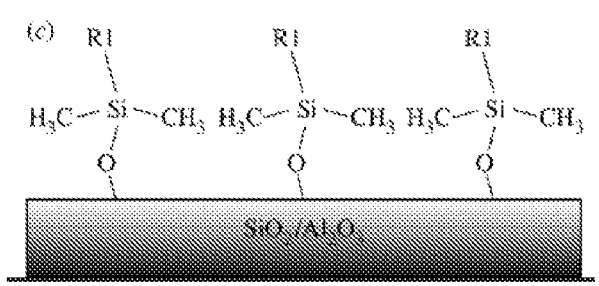
FIG. 2 depicts a non-limiting example of a protein-reactive coating on the surface of an alumina substrate.
Figure 3:
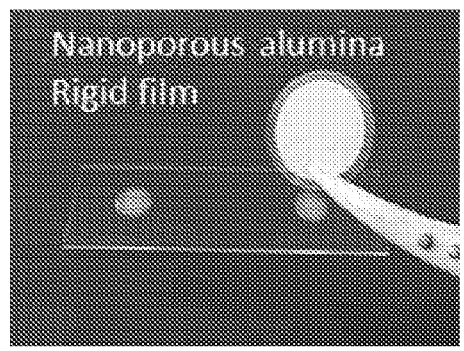
FIG. 3 depicts an embodiment of the invention in the form of a rigid alumina disc.

The porous substrate may be composed of any material that can be engineered to hold the necessary shape and that may accommodate the protein-reactive coating. In various embodiments, the porous substrate comprises nanoporous alumina or porous glass. The porous substrate and the interstices may have any dimensions that can accommodate flow of proteins or a solution containing proteins from one side of the substrate to the other. The interstices may have a diameter of about 500 nm or less than about 500 nm. The porous substrate may have a thickness from the first side to the second side of about 100 μm or less than 100 μm, in some embodiments 50 μm or less than 50 μm. In various embodiments, the porous substrate may have a thickness from the first side to the second side of about 50-100 μm The protein-reactive coating may be any substance that can coat the interstices and form a covalent bond to proteins that contact the protein-reactive coating. The protein reactive coating may form one or more covalent bonds to the peptide backbone or to side groups. In various embodiments, the protein reactive coating covalently binds proteins independent of the protein sequence. In various embodiments, the protein-reactive coating may be a silane derivative. In various embodiments, the protein-reactive coating may be covalently bonded to the porous substrate. FIG. 2 shows an embodiment of the invention comprising a silane derivative protein-reactive coating covalently bonded to a porous alumina substrate. In various embodiments the protein-reactive coating is:

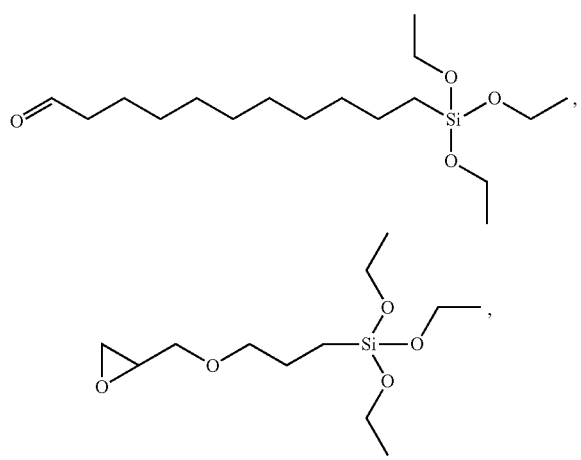

-continued

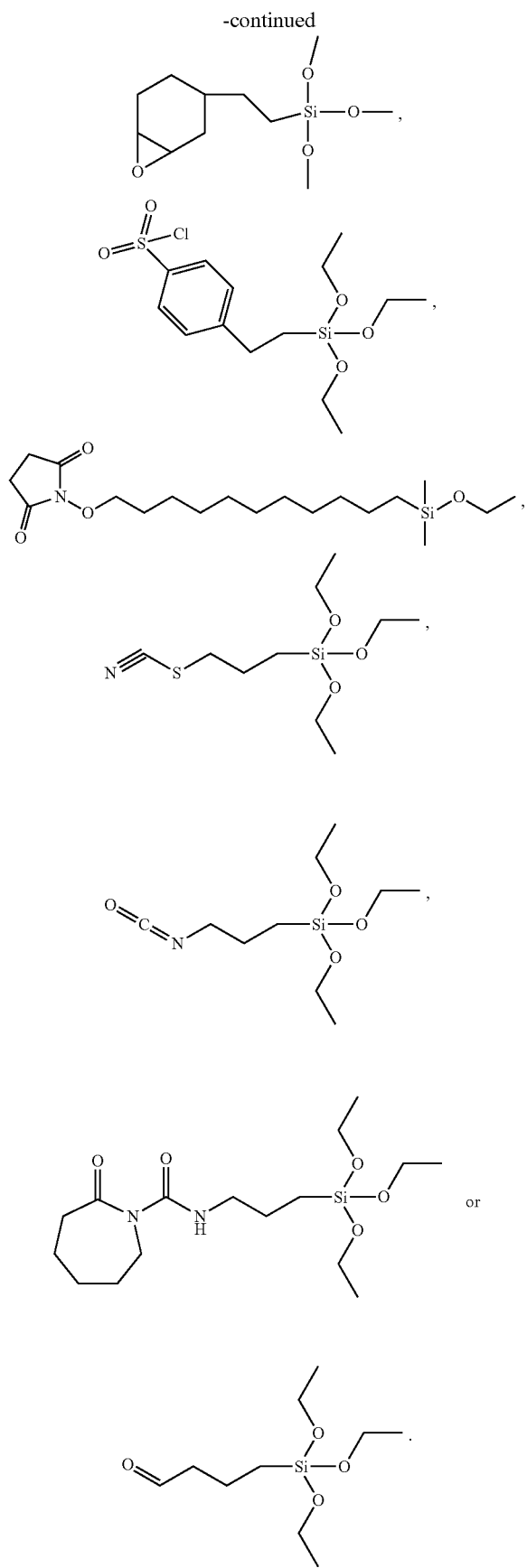

In various embodiments, the protein-reactive coating is triethoxysilylundecanal

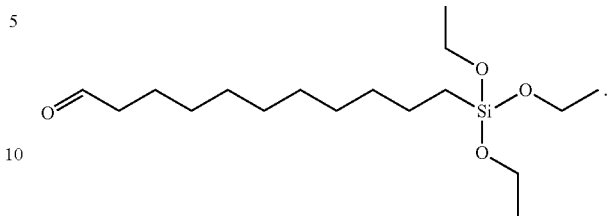

In various embodiments, the protein-reactive coating is selected from the group consisting of 3-thiocyanatopropyl-triethoxysilane, triethoxysilylundecanal, trimethoxy[2-(7-oxabicyclo[4.1.0]hept-3-yl)ethyl]silane, (3-glycidyloxypropyl)triethoxysilane, 3-isocyanatopropyltriethoxysilane, N-[5-(trimethoxysilyl)-2-aza-1-oxopentyl]caprolactam, 11-(succinimidyloxy)undecyl dimethylethoxysilane, 2-(4-chlorosulfonylphenyl)ethyltrimethoxy-silane and triethoxysilyl-butyraldehyde.

Method of Detecting a Protein of Interest

In another aspect, the invention provides a method of detecting at least one protein of interest in a plurality of proteins by contacting the plurality of proteins with a porous substrate having a first side and a second side, and a plurality of interstices extending contiguously from the first side to the second side, wherein the interstices are coated with a protein-reactive coating, thereby covalently binding at least a portion of the plurality of proteins to the protein-reactive coating, exposing the covalently bound plurality of proteins to a first molecule that binds the at least one protein of interest; and detecting the first molecule that binds at least one protein of interest, thereby detecting the at least one protein of interest. The methods of the invention allow the detection of one or more proteins in a complex mixture of proteins, by way of non-limiting example, crude cell lysate. The method may be performed using a small sample. In various embodiments, the plurality of proteins may have a volume of less than 10 μL, less than 5 μL, less than 3 μL or less than 1 μL.

Figure 13:
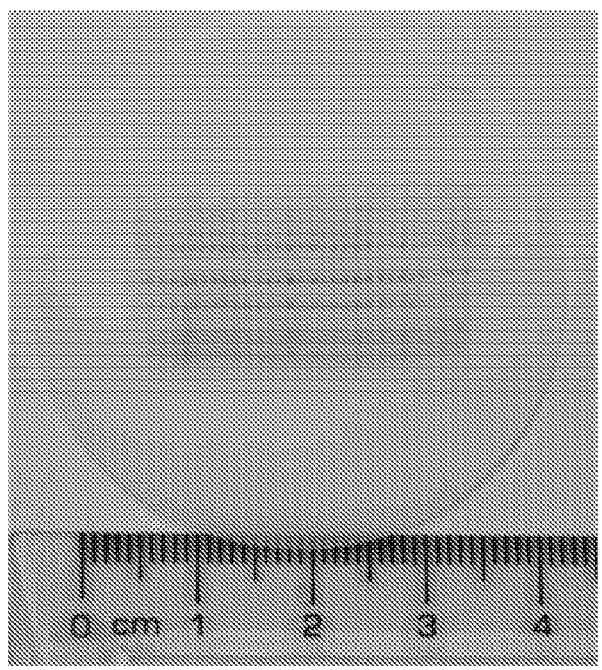
FIG. 13 depicts parallelized micro-scale electrophoretic covalent deposition.
Figure 14:
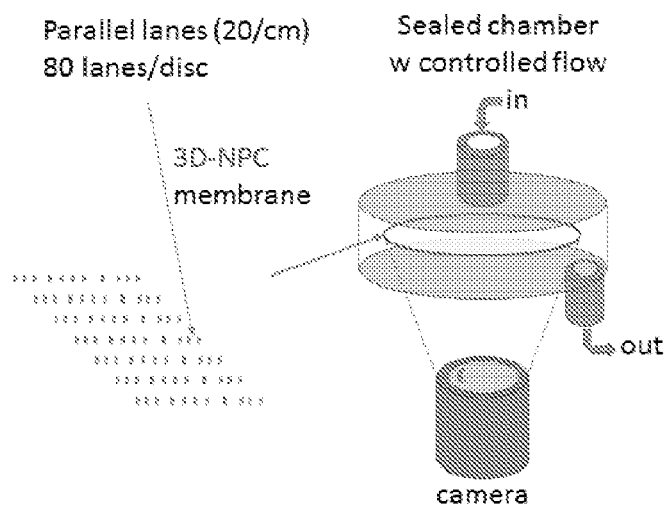
FIG. 14 an embodiment of the invention in which the protein capture membrane is placed in a chamber with an inlet and an outlet chamber to facilitate flow of complex mixtures of proteins, rinse and molecules for detecting bound protein of interest. The figure further shows multiple pluralities of proteins transferred to the membrane.
Figure 15:
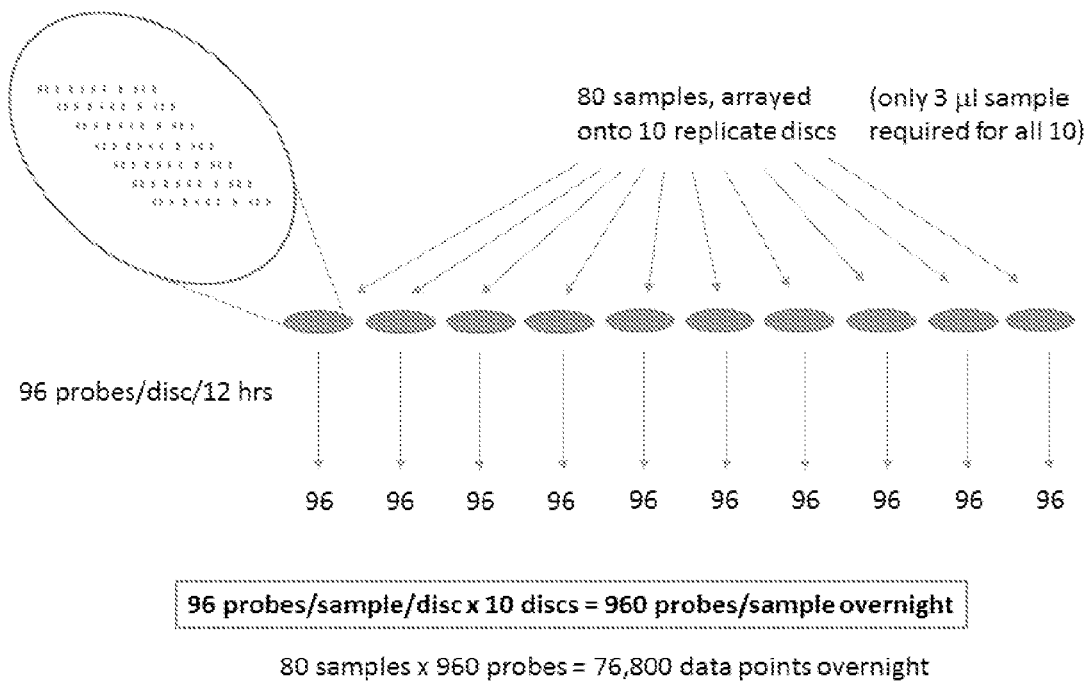
FIG. 15 illustrates high throughput protein detection using an embodiment of the invention.
Figure 16:
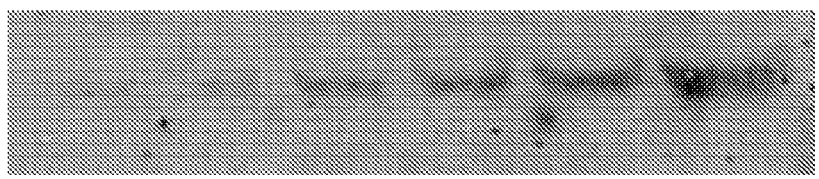
FIG. 16 depicts glass fiber filters (1.6 μm pore size, hydrophilic glass fiber, 47 mm diameter) etched with piranha solution, coated with 2% tiethoxysilylundecanal in THF. Proteins transferred from gel onto derivatized porous glass fiber by electrophoresis, probed with anti-pyk2 antibody. Proteins are transferred and bound effectively to derivatized porous glass, able to be probed and detected with specific antibody.

Contacting the plurality of proteins covalently bound to the porous substrate with a first molecule that binds the at least one protein of interest may be achieved by passive diffusion. In other embodiments, this may be achieved by creating a flow through the interstices using pressure. In other embodiments, this may be achieved by electrophoresis. By way of non-limiting example, FIG. 10 depicts an embodiment in which flow is created by a pair of syringes. Various separation techniques may be employed as part of the contacting step in order to stratify a complex mixture of proteins. In various embodiments, contacting further comprises electrophoretic mobilization of the plurality of proteins. By way of non-limiting example, electrophoretic separation may be sodium-dodecyl sulfate polyacrylamide gel electrophoresis (SDS-PAGE). Contacting may also include electrophoretic transfer of the plurality of proteins to the porous substrate. FIG. 6 depicts an embodiment of the invention in which the plurality of proteins is electrophoretically transferred to the porous substrate following electrophoretic separation. This may allow multiple separate spatially resolved pluralities of proteins (by way of non-limiting example, various bands originating from the same or different wells of the gel) to be transferred and subsequently analyzed. As depicted in FIGS. 13-15, this feature allows multiplexing which may vastly improve throughput.

Exposing the covalently bound plurality of proteins to molecules that bind the protein of interest may include generating a flow of solution containing the molecules through the interstices such that the molecules may bind the protein of interest. The flow may be created by diffusion or by using pressure or by using electrophoretic force. This may be the same as or different from the method used to contact the porous substrate with the plurality of proteins. Molecules that bind the protein of interest may be any molecule that specifically binds to the protein of interest and is detectable thereafter using any means known in the art, by way of non-limiting example, fluorescence. In various embodiments, the first molecule that binds the protein of interest may be an antibody, an aptamer or a protein.

The molecules that bind proteins of interest may be detected by any appropriate means known in the art. In various embodiments, detection of the molecule that binds the protein of interest may require the application of a second reagent, by way of non-limiting example a secondary antibody. In various embodiments, depending on the nature of the molecule that binds the protein of interest, one or more rinsing steps may be performed. Rinsing steps may be necessary or preferable in order to, by way of non-limiting example, lower background due to non-specific binding.

The covalent binding of the plurality of proteins to the protein-reactive coating allows repeated analysis of the same sample. In various embodiments the method further includes steps of stripping the first molecule that binds at least one protein of interest and exposing the covalently bound plurality of proteins to a second molecule that binds the same or a different protein of interest; and detecting the second molecule, thereby detecting the at least one protein of interest. Stripping and re-probing as described here may be repeated more than once. In various embodiments, molecules that bind proteins of interest present in the plurality of proteins may be stripped and new molecules that bind the same or different proteins of interest may be applied, three times, five times, ten times or more. In various embodiments, the second or subsequent molecule is an antibody, an aptamer or a protein. In various embodiments, depending on the nature of the molecule that binds the protein of interest, one or more rinsing steps may be performed during or after stripping and prior to applying a second molecule that binds the same or a different protein of interest.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting at least one protein of interest in a plurality of proteins, the method comprising:
    electrophoretically transferring the plurality of proteins to a porous substrate comprising:
        a first side and a second side, and
        a plurality of interstices extending contiguously from the first side to the second side,
        wherein the interstices are coated with a protein-reactive coating,
    thereby covalently binding at least a portion of the plurality of proteins to the protein-reactive coating,
    exposing the covalently bound plurality of proteins to a first molecule that binds the at least one protein of interest; and
    detecting the first molecule that binds the at least one protein of interest, thereby detecting the at least one protein of interest.

2. The method according to claim 1, wherein the porous substrate comprises nanoporous alumina or porous glass.

3. The method according to claim 1, wherein the first molecule is selected from the group consisting of an antibody, an aptamer and a protein.

4. The method according to claim 1, wherein the method comprises:
    separating the plurality of proteins using electrophoresis prior to transferring to the porous substrate.

5. The method according to claim 1, further comprising:
    stripping the first molecule that binds at least one protein of interest and exposing the covalently bound plurality of proteins to a second molecule that binds the same or a different protein of interest; and
    detecting the second molecule, thereby detecting the at least one protein of interest.

6. The method according to claim 5, wherein the second molecule is selected from the group consisting of an antibody, an aptamer and a protein.

* * * * *